(12) United States Patent
Ream et al.

(10) Patent No.: US 7,078,052 B2
(45) Date of Patent: Jul. 18, 2006

(54) PHARMACEUTICAL CHEWING GUM FORMULATIONS

(75) Inventors: Ronald L. Ream, Plano, IL (US); Christine L. Corriveau, Orlando Park, IL (US); William J. Wokas, Bolingbrook, IL (US); Thomas M. Tongue, Jr., Joliet, IL (US); Michael J. Greenberg, Northbrook, IL (US)

(73) Assignee: Wm. Wrigley Jr. Company, Chicago, IL (US)

( * ) Notice: Subject to any disclaimer, the term of this patent is extended or adjusted under 35 U.S.C. 154(b) by 0 days.

(21) Appl. No.: 10/743,609

(22) Filed: Dec. 22, 2003

(65) Prior Publication Data

US 2004/0180007 A1  Sep. 16, 2004

Related U.S. Application Data

(60) Continuation of application No. 09/671,552, filed on Sep. 27, 2000, now abandoned, which is a division of application No. 09/286,818, filed on Apr. 6, 1999.

(51) Int. Cl.
*A61K 9/68* (2006.01)

(52) U.S. Cl. .................. 424/440; 424/48; 424/439; 424/441

(58) Field of Classification Search ............. 424/48, 424/439, 440; 426/3, 5, 6
See application file for complete search history.

(56) References Cited

U.S. PATENT DOCUMENTS

| | | |
|---|---|---|
| 3,554,767 A | 1/1971 | Daum |
| 3,995,064 A | 11/1976 | Ehrgott et al. |
| 4,238,510 A | 12/1980 | Cherukuri et al. |
| 4,250,195 A | 2/1981 | Cherukuri et al. |
| 4,283,408 A | 8/1981 | Hirata et al. |
| 4,317,838 A | 3/1982 | Cherukuri et al. |
| 4,374,858 A | 2/1983 | Glass et al. |
| 4,378,374 A | 3/1983 | Reggio et al. |
| 4,386,106 A | 5/1983 | Merritt et al. |
| 4,446,135 A | 5/1984 | Fountaine |
| 4,459,311 A | 7/1984 | DeTora et al. |
| 4,555,407 A | 11/1985 | Kramer et al. |
| 4,882,152 A | 11/1989 | Yang et al. |
| 4,968,511 A | 11/1990 | D'Amelia et al. |

(Continued)

FOREIGN PATENT DOCUMENTS

DE   43 42 568   6/1984

(Continued)

OTHER PUBLICATIONS

Aspergum®, advertisement from the web ste www.drugstore.com.*

(Continued)

*Primary Examiner*—S. Tran
(74) *Attorney, Agent, or Firm*—Bell, Boyd & Lloyd LLC (57) ABSTRACT

Methods and chewing gums for delivering a medicament or agent to an individual are provided. The chewing gum includes a medicament or agent. The medicament or agent is present within the chewing gum composition (the water soluble portion and/or insoluble base portion). It has been found that by chewing the gum, the medicament or agent is released from the chewing gum. Continuing to chew the chewing gum creates a pressure within the buccal cavity forcing the agent or medicament directly into the systemic system of the individual through the oral mucosa contained in the buccal cavity. This greatly enhances the absorption of the drug into the systemic system as well as the bioavailability of the drug within the system.

5 Claims, 3 Drawing Sheets

U.S. PATENT DOCUMENTS

| | | | |
|---|---|---|---|
| 5,045,325 A | 9/1991 | Lesko et al. | |
| 5,110,608 A | 5/1992 | Cherukuri et al. | |
| 5,139,794 A | 8/1992 | Patel et al. | |
| 5,229,137 A | 7/1993 | Wolfe | |
| 5,244,670 A | 9/1993 | Upson et al. | |
| 5,286,500 A | 2/1994 | Synosky et al. | |
| 5,294,433 A | 3/1994 | Singer et al. | |
| 5,397,580 A | 3/1995 | Song et al. | |
| 5,419,919 A | 5/1995 | Song et al. | |
| 5,523,097 A | 6/1996 | Song et al. | |
| 5,536,511 A | 7/1996 | Yatka | |
| 5,543,160 A | 8/1996 | Song et al. | |
| 5,569,477 A | 10/1996 | Nesbitt | |
| 5,571,543 A | 11/1996 | Song et al. | |
| 5,576,344 A | 11/1996 | Sandler et al. | |
| 5,601,858 A | 2/1997 | Mansukhani et al. | |
| 5,629,013 A | 5/1997 | Upson et al. | |
| 5,629,026 A | 5/1997 | Davis | |
| 5,651,987 A | 7/1997 | Fuisz | |
| 5,656,652 A | 8/1997 | Davis | |
| 5,665,406 A | 9/1997 | Reed et al. | |
| 5,800,847 A | 9/1998 | Song et al. | |
| 5,854,267 A | 12/1998 | Berlin et al. | |
| 5,858,383 A | 1/1999 | Precopio | |
| 5,858,412 A | 1/1999 | Staniforth et al. | |
| 5,858,413 A | 1/1999 | Jettka et al. | |
| 5,858,423 A | 1/1999 | Yajima et al. | |
| 5,889,028 A | 3/1999 | Sandborn et al. | |
| 5,980,955 A | 11/1999 | Grennberg et al. | |
| 5,989,588 A | 11/1999 | Korn et al. | |
| 6,024,988 A | 2/2000 | Ream et al. | |
| 6,066,342 A | 5/2000 | Gurol et al. | |
| 6,077,524 A | 6/2000 | Bolder et al. | |
| 6,090,412 A | 7/2000 | Hashimoto et al. | |
| 6,165,516 A | 12/2000 | Gudas et al. | |
| 6,200,604 B1 | 3/2001 | Pather et al. | |
| 6,242,018 B1 * | 6/2001 | Fahey et al. | 426/49 |
| 6,258,376 B1 | 7/2001 | Athanikar | |
| 6,290,985 B1 | 9/2001 | Ream et al. | |
| 6,322,806 B1 | 11/2001 | Ream et al. | |
| 6,350,480 B1 | 2/2002 | Urnezis et al. | |
| 6,355,265 B1 | 3/2002 | Ream et al. | |
| 6,413,558 B1 * | 7/2002 | Weber et al. | 426/2 |
| 6,429,198 B1 * | 8/2002 | St. Cyr et al. | 514/23 |
| 6,444,241 B1 | 9/2002 | Tyrpin et al. | |
| 6,465,003 B1 | 10/2002 | Ream et al. | |
| 6,531,114 B1 | 3/2003 | Gmunder et al. | |
| 6,541,048 B1 | 4/2003 | Zyck et al. | |
| 6,558,692 B1 | 5/2003 | Ream et al. | |
| 6,569,472 B1 | 5/2003 | Zyck et al. | |
| 6,572,900 B1 | 6/2003 | Zyck et al. | |
| 6,579,545 B1 | 6/2003 | Zyck et al. | |
| 6,586,023 B1 * | 7/2003 | Song et al. | 426/5 |
| 6,613,346 B1 | 9/2003 | Seilstad et al. | |
| 6,627,234 B1 | 9/2003 | Johnson et al. | |
| 6,645,535 B1 | 11/2003 | Zyck et al. | |
| 6,663,849 B1 | 12/2003 | Zyck et al. | |

FOREIGN PATENT DOCUMENTS

| | | |
|---|---|---|
| EP | 0 221 850 A2 | 5/1987 |
| EP | 0 273 809 B1 | 7/1998 |
| FR | 2 635 441 | 2/1990 |
| GB | 0 934 596 | 8/1963 |
| GB | 0 963 518 | 7/1964 |
| GB | 1 489 832 | 10/1977 |
| IT | 0217487 | 7/1997 |
| JP | 91-251533 | 11/1991 |
| JP | 94-303911 | 11/1994 |
| JP | 96-19370 | 1/1996 |
| JP | 86/242561 | 10/1996 |
| KR | 94-2868 | 4/1994 |
| RU | 2029474 C1 | 2/1995 |
| WO | WO 95/00038 | 1/1995 |
| WO | WO 95/00039 | 1/1995 |
| WO | WO 95/10290 | 4/1995 |
| WO | WO 96/00070 | 1/1996 |
| WO | WO 97/21424 | 6/1997 |
| WO | WO 97/24036 | 7/1997 |
| WO | WO 98/12933 | 4/1998 |
| WO | WO 9823165 A1 * | 6/1998 |
| WO | WO 99/27798 | 6/1999 |
| WO | WO 99/44436 | 9/1999 |
| WO | WO 00/13523 | 3/2000 |
| WO | WO 00/35296 | 6/2000 |
| WO | WO 00/35298 | 6/2000 |
| WO | WO 00/38532 | 7/2000 |

OTHER PUBLICATIONS

Dr. Massimo Calanchi and Dr. Sam Ghanta, "Taste-masking of oral formulations", Eurand International SpA, Pharmaceutical Manufacturing International, 1996 (5 pages).

Merck Index, 11$^{th}$ Ed., #1635 "Caffeine" (1989), p. 248.

Merck Index, 12$^{th}$ Ed., #2337 "Cimetidine" (1996), p. 383.

Merck Index, 12$^{th}$ Ed., #3264 "Dimethicone" (1996), p. 544.

Merck Index, 12$^{th}$ Ed., #3972 "Famotidine" (1996), p. 667.

Merck Index, 12$^{th}$ Ed., #6758 "Nizatidine" (1996), p. 1143.

Merck Index, 12$^{th}$ Ed., #6977 "Omeprazole" (1996), p. 1174.

Merck Index, 12$^{th}$ Ed., #8272 "Raberprazole" (1996), p. 1392.

Merck Index, 12$^{th}$ Ed., #8286 "Ranitidine" (1996), p. 1395.

James G. Elliott, "Application of Antioxidant Vitamins in Foods and Beverages" Food Technology, (Feb. 1999), pp. 46-48.

C. Curtis Vreeland, "Nutraceuticals Fuel Confectionery Growth" Candy R&D, (Mar. 1999), pp. 29, 31-32, 34-35.

Kitty Broihier, R.D., "Foods of Tomorrow, Milking The Nutrition Market", Food Processing, (Mar. 1999), pp. 41, 42 and 44.

Kitty Broihier, R.D., "Tea Time For Nutraceuticals, New Black, Green Tea Products Brew Up a Bevy Of Health Benefits", Food Processing; (Mar. 1999), pp. 59, 61 and 63.

Andrea Allen, Jack Neff, Lori Dahm and Mary Ellen Kuhn, "Exclusive Guide to Wellness Foods and Nutraceuticals", Food Processing (Special Supplement), (Mar. 1999).

Product package "Aspergum" distributed by Heritage Consumer Products, LLC (on sale prior to Nov. 27, 1995).

Product package "Dental Care the Baking Soda Gum" distributed by Church & Dwight Co., Inc. (1998).

Product package "BreathAsure Dental Gum" distributed by Breath Asure, Inc. (1998).

Product package "Trident Advantage with Baking Soda" distributed by Warner-Lambert Co. (1998).

The United States Pharmacopeia The National Formulary—"General Information", dated Jan. 1, 1990 pp. 1624-1625 and pp. 1696-1697.

Product package for Stay Alert Caffeine Supplement Gum, distributed by Amurol Confections Company (first quarter 1998).

Specialty Minerals Inc. Brochure (Apr. 1998), (19 pages).

Beckett, A.H., et al., "Buccal absorption of basic drugs and its application as an in vivo model of passive drug transfer through lipid membranes" (1967) J. Pharm. Pharmac., 19 Suppl. 31S-41S.

Weinberg, David S., et al. "Sublingual absorption of selected opioid analgesics" (1988) Clin. Pharmacol Ther., 44:335-342.

"The Basic Clinical Pharmacology," vol. 1, p. 75, 1998 edited by Bertram G. Katzung.

* cited by examiner

PHARMACEUTICAL CHEWING GUM FORMULATIONS

This application is a Continuation of prior application Ser. No. 09/671,552, filed Sep. 27, 2000, now abandoned Which is a Divisional of prior application Ser. No. 09/286,818, filed Apr. 6, 1999.

BACKGROUND OF THE INVENTION

The present invention generally relates to the delivery of medicaments and other agents. More specifically, the present invention relates to the delivery of medicaments and agents using chewing gum formulations.

It is of course known to provide agents to individuals for various purposes. These agents can be used to treat diseases and as such are typically referred to as drugs or medicaments. Likewise, the drugs or medicaments can be used for prophylactic purposes. Still, it is known to provide agents to an individual for a variety of non-medical purposes including enhancing performance or maintaining or initiating alertness.

There are a great variety of such agents. These agents run the gamut from stimulants such as caffeine to drugs such as analgesics, tranquilizers, cardiovascular products, insulin, etc. Some such agents are taken on an as needed basis while other agents must be taken at regular intervals by the individual.

Typically, drugs (medicaments) are administered parenterally or enterally. Of course, parenteral administration is the administration of the drug intravenously directly into the blood stream. Enteral refers to the administration of the drug into the gastrointestinal tract. In either case, the goal of the drug administration is to move the drug from the site of administration towards the systemic circulation.

Except when given intravenously, a drug must traverse several semipermeable cell membranes before reaching general circulation. These membranes act as a biological barrier that inhibits the passage of drug molecules. There are believed to be four processes by which drugs move across a biological barrier: passive diffusion; facilitated diffusion; active transport; and pinocytosis.

Passive diffusion is the transport across the cell membrane wherein the driving force for the movement is the concentration gradient of the solute. In orally administered drugs, this absorption occurs in the small intestines. Facilitated diffusion is believed to be based on a carrier component that combines reversibly with the substrate molecule at the cell membrane exterior. The carrier substrate complex diffuses rapidly across the membrane with release of the substrate at the interior surface. Active transport requires an energy expenditure by the cell and appears to be limited to agents with structural similarities to normal body constituents. These agents are usually absorbed from specific sites in the small intestines. Pinocytosis refers to the engulfing of particulars or fluid by a cell. It is believed to play a minor role in drug transport. *Merck Manual*, 16th Edition, pp. 2598–2599.

In determining the efficacy of a drug and the effectiveness of the use of a drug to treat a disease, drug absorption is a critical concern. Drug absorption refers to the process of drug movement from the site of administration toward the systemic circulation.

Oral administration of drugs is by far the most common method. When administered orally, drug absorption usually occurs due to the transport of cells across the membranes of the epithelial cells within the gastrointestinal tract. Absorption after oral administration is confounded by numerous factors. These factors include differences down the alimentary cannel in: the luminal pH; surface area per luminal volume; perfusion of tissue, bile, and mucus flow; and the epithelial membranes. See *Merck Manual* at page 2599.

A further issue effecting the absorption of orally administered drugs is the form of the drug. Most orally administered drugs are in the form of tablets or capsules. This is primarily for convenience, economy, stability, and patient acceptance. Accordingly, these capsules or tablets must be disintegrated or dissolved before absorption can occur. There are a variety of factors capable of varying or retarding disintegration of solid dosage forms. Further, there are a variety of factors that effect the dissolution rate and therefore determine the availability of the drug for absorption. See *Merck Manual* at page 2600.

Parental administration allows for the direct placement of the drug into the blood stream. This usually insures complete delivery of the dose to the general circulation. However, administration by a route that requires drug transfer through one or more biologic membranes to reach the blood stream precludes a guarantee that all of the drug will eventually be absorbed. Even with parental administration, because capillaries tend to be highly porous, the perfusion (blood flow/gram of tissue) is a major factor in the rate of absorption. Thus, the injection site can markedly influence a drugs' absorption rate; e.g., the absorption rate of diazepam injected IM into a site with poor blood flow can be much slower than following an oral dose. See *Merck Manual* at page 2601.

Not only is drug absorption an issue in drug delivery but also the bioavailability of the drug is also critical. Bioavailability is defined as the rate at which and the extent to which the active moiety (drug or metabolite) enters the general circulation, thereby gaining access to the site of action. Bioavailability depends upon a number of factors, including how a drug product is designed and manufactured, its physicochemical properties, and factors that relate to the physiology and pathology of the patient. See *Merck Manual* at page 2602.

When a drug rapidly dissolves from a drug product and readily passes across membranes, absorption from most site administration tends to be complete. This is not always the case for drugs given orally. Before reaching the vena cava, the drug must move down the alimentary cannel and pass through the gut wall and liver, which are common sites of drug metabolism. Thus, the drug may be metabolized before it can be measured in the general circulation. This cause of a decrease in drug input is called the first pass effect. A large number of drugs show low bioabilities owing to an extensive first pass metabolism. The two other most frequent causes of low bioavailability are insufficient time in the GI tract and the presence of competing reactions. See *Merck Manual* at page 2602.

Bioavailability considerations are most often encountered for orally administered drugs. Differences in bioavailability can have profound clinical significance.

Although parental administration does provide a method for eliminating a number of the variables that are present with oral administration, parental administration is not a preferable route. Typically, parental administration requires the use of medical personnel and is just not warranted nor practical for the administration of most agents and drugs, e.g., analgesics. Even when required parenteral administration is not preferred due to patient concerns including comfort, infection, etc., as well as the equipment and costs involved. However, despite best efforts certain therapies require parenterally injected drugs. For example, research for decades has focused on an attempt to deliver insulin to an individual through a non-parental means. Despite such efforts today insulin is still only administered intravenously.

There is therefore a need for an improved method of delivering drugs and agents to an individual.

SUMMARY OF THE INVENTION

The present invention provides improved methods for delivering a medicament or agent to an individual. To this end, chewing gum is provided including a medicament or agent. The medicament or agent is present within the chewing gum composition (the water soluble portion and/or insoluble base portion). It has been found that by chewing the gum, the medicament or agent is released from the chewing gum. Continuing to chew the chewing gum creates a pressure within the buccal cavity forcing the agent or medicament directly into the systemic system of the individual through the oral mucosa contained in the buccal cavity. This greatly enhances the absorption of the drug into the systemic system as well as the bioavailability of the drug within the system.

Improved chewing gum formulations including medicaments and agents are also provided by the present invention.

To this end, the present invention provides a method of drug delivery comprising the steps of: providing a chewing gum that includes a medicament in the chewing gum composition; chewing the chewing gum to cause the medicament to be released from the chewing gum composition into the buccal cavity of the chewer; and continuing to chew the chewing gum thereby creating a fluid pressure causing the medicament to enter the systemic system of the chewer through the oral mucosa contained in the buccal cavity.

In an embodiment, the chewing gum is chewed for at least 2 minutes.

In an embodiment, the medicament is chosen from the group consisting of: analgesics; muscle relaxants; antacids; antihistamines; decongestants; anti-inflammatories; antibiotics; antivirals; psychotherapeutic agents; insulin; and cardiovascular agents.

In an embodiment, the chewing gum including the medicament is chewed at least twice a day.

In an embodiment, two pieces of chewing gum are chewed at a time.

In a further embodiment, the present invention provides a method for reducing the amount of agent necessary to achieve an effect in an individual as compared to a typical agent that is swallowed. The method comprises the steps of: providing a chewing gum including an agent that is typically swallowed by an individual to achieve a specific effect, the chewing gum including less than the typical amount of agent that is swallowed by the individual to achieve the effect; chewing the chewing gum and thereby causing the agent to be released into the salvia of the individual; and continuing to chew the chewing gum forcing the agent through the mucous membranes in a buccal cavity of the individual.

In an embodiment of the method, the agent is a medicament.

In an embodiment of the method, the medicament is chosen from the group consisting of: analgesics; muscle relaxants; antihistamines; decongestants; antacids; anti-inflammatories; antibiotics; antivirals; psychotherapeutic agents; and cardiovascular agents.

In an embodiment of the method, the chewing gum is chewed for at least 2 minutes.

In an embodiment of the method, the chewing gum creates a saliva content of agent of at least 0.5 to about 5000 ppm depending on the medicament.

In an embodiment of the method, the agent is a stimulant.

In another embodiment, the present invention provides a method of enhancing an individual's performance comprising the steps of: providing chewing gum including a performance enhancing amount of caffeine; and chewing the chewing gum not more than ten minutes before the performance.

In an embodiment, the performance to be enhanced is athletic.

In an embodiment, the performance to be enhanced is cognitive.

In an embodiment, the performance to be enhanced is alertness.

In an embodiment, the chewing gum is chewed not more than 5 minutes before the performance.

In still a further embodiment, the present invention provides a method of delivering a medicament comprising the steps of: providing a chewing gum including a medicament; and chewing the chewing gum for at least 2 minutes.

In an embodiment, the medicament is chosen from the group consisting of:

analgesics; muscle relaxants; antihistamines; decongestants; antacids; anti-inflammatories; antibiotics; antivirals; psychotherapeutic agents; insulin; and cardiovascular agents.

Yet further, the present invention provides a method of increasing the stimulatory effect of a stimulant that has been previously ingested by an individual comprising the steps of: providing a chewing gum that contains the stimulant; and chewing the chewing gum causing the stimulant to be released by the chewing gum and forced into the oral mucosa of the individual.

Accordingly, an advantage of the present invention is to provide new methods for delivering medicaments or agents to an individual.

Still further, an advantage of the present invention is to provide a method of delivering medicaments to an individual that provides for increase absorption and bioavailability as compared to medicaments that are designed to be absorbed in the GI tract.

Further, an advantage of the present invention is to provide a method of administering a medicament or agent to an individual at a lower level than is typically administered orally while still achieving the same effect.

Furthermore, an advantage of the present invention is to provide a method for administering drugs or agents to an individual that heretofore were administered parentally.

Additionally, an advantage of the present invention is to provide a method for administering drugs that is more palatable than current methods.

Another advantage of the present invention is to provide a method for enhancing the performance of an individual through the administration of an agent.

Moreover, an advantage of the present invention is to provide an improved method for drug delivery.

Still, an advantage of the present invention is to provide a method for creating a triggering effect that creates a synergistic effect with an agent that is present in the systemic circulation of the individual.

Additional features and advantages of the present invention will be described in and apparent from the detailed description of the presently preferred embodiments and the figures.

DETAILED DESCRIPTION OF THE PRESENTLY PREFERRED EMBODIMENTS

The present invention provides improved methods for delivering medicaments and other agents to an individual as well as improved formulations including such medicaments and agents. Pursuant to the present invention, a medicament or agent is contained in a chewing gum formulation. In contrast to prior such formulations, the medicament or agent is contained directly in the chewing gum composition, e.g., not in. a coating around the chewing gum.

Accordingly, as the chewing gum is chewed, the medicament or agent is released into the saliva. During continual chewing, the medicament or agent in the saliva is then forced due to the pressure created by the chewing through the oral mucosa in the buccal cavity. The oral mucosa has a thin epithelium and a rich vascularity. Thus, the oral mucosa favors drug absorption. In contrast to a typically orally ingested drug, wherein the solution is in contact too briefly for absorption to be appreciable through the oral mucosa, it is believed that during chewing, the agent and/or medicament remains in the buccal cavity and is forced through the oral mucosa. Also it has been surprisingly found that an increase in the absorption of the drug is achieved as well as an increase in the bioavailability of the drug as compared to typical oral administration. It has been found that the drug or agent is absorbed much quicker than if it was swallowed as in a typical oral administration. Indeed, the absorption approaches that of a parental administration, and bioavailability is also much greater than oral administration.

It has also been surprisingly found that less medicament or agent can be placed in the chewing gum than is typically orally administered to an individual to achieve an effect and the same bioequivalence can be achieved. In fact, it has been surprisingly found that in certain instances, for at least certain drugs and agents, the administration of the medicament or agent using chewing gum through the buccal cavity can provide an increase effect even as compared to parenteral administration.

For example, caffeine is commonly used as a stimulant to alleviate the effects of sleep deprivation. It is almost completely metabolized in the liver and therefore classified as a low clearance, flow independent drug. This means its rate of inactivation is unaffected by delivery to the liver and can only be modified by a change in the hepatic enzyme activity.

The pharmacokinetics of caffeine have been well documented and there is no significant difference between oral and intravenous administration. However, data set forth in detail below, suggests that the absorption rate constant (Ka) is significantly increased when caffeine is administered through chewing gum. This means that the caffeine is moving into the systemic circulation at a significantly faster rate. A similar change in the onset of dynamic response has also been noted, e.g., alertness and performance.

It has additionally been surprisingly found that for at least certain agents that placing the agent in the chewing gum can have a triggering effect on the agent that may be in the systemic circulation. For example, it has been found that with respect to caffeine that is ingested orally, that after the ingestion of a certain amount of caffeine, and the elapse of a certain period of time, that further ingestion of caffeine has a negligible effect on the individual. However, upon chewing gum with caffeine there has been observed a triggering effect that appears to create a synergistic effect with the caffeine that is in the systemic circulation. It is believed that this triggering effect will also be present with other agents, e.g., analgesics.

It is envisioned, that a variety of different medicaments and agents can be used in the chewing gum. For example, such agents include, inter alia, stimulants such as caffeine. Generally, such medicaments include, inter alia, analgesics, antibiotics, antivirals, antihistamines, anti-inflammatories, decongestants, antacids, muscle relaxants, psychotherapeutic agents, insulin, and cardiovascular agents. It is envisioned, that depending on the medicament, the resultant chewing gum can be used to treat, inter alia: coughs; colds; motion sickness; allergies; fevers; pain; inflammation; sore throats; cold sores; sinus problems; diarrhea; diabetics; depression; anxiety; and other maladies and symptoms. Specific agents/medicaments include, by way of example and not limitation: caffeine; aspirin; acetaminophen; ibuprofen; hydroxycitric acid; chromium picolinate; phosphatidylserine; nicotine; insulin; *Echinacea purpurea;* zinc; vitamin C; ginseng; kola nut; kaua kaua; and chamomile.

Preferably, the agents or medicaments are contained in the chewing gum formulation at levels of approximately 50 micrograms to 500 milligrams. The specific levels will depend on the active ingredient. For example, if chromium picolinate is the active ingredient in an embodiment, it would be present at a level of 50 micrograms per serving (2.8 grams stick of gum); aspirin would be preset at a level of 325 milligrams per 2.8 gram serving (stick).

The level of medicament or agent in the chewing gum formulation is selected so as to create, when the gum is chewed, a sufficiently high concentration of the medicament or agent in the saliva.

For example, when the agent is a stimulant such as nicotine or caffeine, the level of the stimulant in the chewing gum should be such that it creates a saliva content of stimulant of approximately 15 to 440 ppm when the chewing gum is chewed for 2 minutes. At this level, a sufficient amount of stimulant will be delivered to the chewer to create the effects set forth in the application. If a medicament is used such as a medicinal (e.g., analgesics), sufficient medicinal should be present in the chewing gum to create a salvia content of approximately 1700 to approximately 4400 ppm after the chewing gum has been chewed for 2 minutes. For a botanicals (e.g., chamomile, kava, kola, nut, ginseng, and *Echinacea*), the agent should be present in a sufficient amount to create a saliva content of approximately 85 to 1100 ppm when the chewing gum is chewed for 2 minutes. For a metabolizer, for example, chromium picolineate and hydroxi-chitic acid, the agents should be present in an amount to create a saliva content of approximately 0.5 to about 900 ppm when chewed for at least two minutes. If the agent is a vitamin or mineral (e.g., phosphatidy serine, vitamin C, and zinc), the agent should be present in the amount to create a saliva content of the vitamin or mineral of approximately 10 to about 250 ppm when chewed for 2 minutes.

Pursuant to the present invention, depending on the agent or medicament, the dosing regiment will change. For example, if the medicament is an analgesic, the chewing gum would be taken on an as needed basis. Of course, similar to the oral administration of an analgesic, there would be restrictions on the number of pieces of chewing gum, chewed, for example, not more often than one stick every four hours and not more often than four to five times a day.

If the agent is a stimulant such as caffeine to be used to enhance performance than the chewing gum would be chewed, in a preferred embodiment ten minutes or less before the performance. As set forth below in the experiment, it has been surprisingly found that another 5 minutes of chewing a chewing gum including caffeine a high level of alertness is achieved.

The medicament or agent can be contained in a variety of different chewing gum compositions. Referring now to the chewing gum, pursuant to the present invention, the chewing gum including the medicament or agent may be based on a variety of different chewing gums that are known. For example, the chewing gums can be low or high moisture, sugar or sugarless, wax containing or wax free, low calorie (via high base or low calorie bulking agents), and/or may contain dental agents.

Chewing gum generally consists of a water insoluble gum base, a water soluble portion, and flavor. The water soluble portion dissipates with a portion of the flavor of the gum over a period of time during chewing. The gum base portion is retained in the mouth throughout the chew.

The insoluble gum base generally comprises elastomers, resins, fats and oils, softeners and inorganic fillers. The gum base may or may not include wax. The insoluble gum base can constitute approximately 5% to about 95% by weight of the chewing gum, more commonly the gum base comprises 10% to about 50% of the gum, and in some preferred embodiments approximately 25% to about 35%, by weight, of the chewing gum.

In an embodiment, the chewing gum base of the present invention contains about 20% to about 60% by weight synthetic elastomer, about 0% to about 30% by weight natural elastomer, about 5% to about 55% by weight elastomer plasticizer, about 4% to about 35% by weight filler, about 5% to about 35% by weight softener, and optional minor amounts (about 1% or less by weight) of miscellaneous ingredients such as colorants, antioxidants, etc.

Synthetic elastomers may include, but are not limited to, polyisobutylene with GPC weight average molecular weight of about 10,000 to about 95,000, isobutylene-isoprene copolymer (butyl elastomer), styrene-butadiene, copolymers having styrene-butadiene ratios of about 1:3 to about 3:1, polyvinyl acetate having GPC weight average molecular weight of about 2,000 to about 90,000, polyisoprene, polyethylene, vinyl acetate—vinyl laurate copolymer having vinyl laurate content of about 5% to about 50% by weight of the copolymer, and combinations thereof.

Preferred ranges for polyisobutylene are 50,000 to 80,000 GPC weight average molecular weight and for styrene-butadiene are 1:1 to 1:3 bound styrene-butadiene, for polyvinyl acetate are 10,000 to 65,000 GBC weight average molecular weight with the higher molecular weight polyvinyl acetates typically used in bubble gum base, and for vinyl acetate-vinyl laurate, vinyl laurate content of 10–45%.

Natural elastomers may include natural rubber such as smoked or liquid latex and guayule as well as natural gums such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva and massaranduba balata.

Elastomer plasticizers may include, but are not limited to, natural rosin esters such as glycerol esters or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium oxide, mono-, di- and tri-calcium phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithin, mono-, di- and triglycerides, acetylated monoglycerides, fatty acids (e.g. stearic, palmitic, oleic and linoleic acids), and combinations thereof.

Colorants and whiteners may include FD&C-type dyes and lakes, fruit and vegetable extracts, titanium dioxide, and combinations thereof.

The base may or may not include wax. An example of a wax-free gum base is disclosed in U.S. Pat. No. 5,286,500, the disclosure of which is incorporated herein by reference.

In addition to a water insoluble gum base portion, a typical chewing gum composition includes a water soluble bulk portion and one or more flavoring agents. The water soluble portion can include bulk sweeteners, high intensity sweeteners, flavoring agents, softeners, emulsifiers, colors, acidulants, fillers, antioxidants, and other components that provide desired attributes.

Softeners are added to the chewing gum in order to optimize the chewability and mouth feel of the gum. The softeners, which are also known as plasticizers and plasticizing agents, generally constitute between approximately 0.5% to about 15% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners include both sugar and sugarless components. Bulk sweeteners typically constitute about 5% to about 95% by weight of the chewing gum, more typically, about 20% to about 80% by weight, and more commonly, about 30% to about 60% by weight of the gum. Sugar sweeteners generally include saccharide-containing components commonly known in the chewing gum art, including but not limited to, sucrose, dextrose, maltose, dextrin, dried invert sugar, fructose, levulose, glactose, corn syrup solids, and the like, alone or in combination. Sugarless sweeteners include, but are not limited to, sugar alcohols such as sorbitol, mannitol, xylitol, hydrogenated starch hydrolysates, maltitol, and the like, alone or in combination.

High intensity artificial sweeteners can also be used, alone or in combination, with the above. Preferred sweeteners include, but are not limited to, sucralose, aspartame, salts of acesulfame, altitame, saccharin and its salts, cyclamic acid and its salts, glycerrhizinate, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Combinations of sugar and/or sugarless sweeteners may be used in chewing gum. Additionally, the softener may also provide additional sweetness such as with aqueous sugar or alditol solutions.

If a low calorie gum is desired, a low caloric bulking agent can be used. Examples of low caloric bulking agents include: polydextrose; Raftilose, Raftilin; Fructooligosaccharides (NutraFlora); Palatinose oligosaccharide; Guar Gum Hydrolysate (Sun Fiber); or indigestible dextrin (Fibersol). However, other low calorie bulking agents can be used.

A variety of flavoring agents can also be used, if desired. The flavor can be used in amounts of about 0.1 to about 15 weight percent of the gum, and preferably, about 0.2% to about 5% by weight. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion.

If the medicament or agent is water soluble in the chewing gum, it preferably will include a base/emulsifier system which leads to the desired concentration of the medicament in the saliva (more hydrophilic balance). If the medicament or agent is water insoluble, the chewing gum preferably includes a base/emulsifier system which leads to the desired concentration of the medicament in the saliva (more lipophilic balance).

In manufacturing the chewing gum including the agent or ingredient, the agent or medicament is added, preferably, early on in the mix. The smaller the amount of active ingredient used, the more necessary it becomes to preblend that particular ingredient to assume uniform distribution throughout the batch of gum. Whether a preblend is used or not, in a preferred embodiment, the agent or medicament should be added within the first five minutes of mixing.

By way of example, and not limitation, examples of some chewing gum formulations including a medicament or agent are as follows:

| ASPIRIN GUM | |
| --- | --- |
| INGREDIENT | PERCENTAGE |
| Sugar | 48.44 |
| Gum Base | 19.50 |
| Corn Syrup | 10.00 |
| Glycerine | 3.00 |
| Aspirin | 12.04 |
| *Caffeine | 1.19 |
| Artificial Flavors | 0.90 |
| Aspartame | 0.23 |
| Fructose | 4.50 |
| Soluble Saccharin | 0.16 |
| Insoluble Saccharin | 0.04 |
| | 100.00 |

2.7 g stick yields 325 mg aspirin and 32 mg caffeine
*FORMULA AVAILABLE EXCLUDING CAFFEINE

| CAFFEINE GUM | |
| --- | --- |
| INGREDIENT | PERCENTAGE |
| Sugar | 56.54 |
| Gum Base | 19.80 |
| Corn Syrup | 8.20 |
| Natural & Artificial Flavors | 3.60 |
| Glycerine | 3.00 |
| Xylitol | 2.90 |
| Dextrose | 2.30 |
| Caffeine | 1.80 |
| Low Fat Cocoa | 1.00 |
| Lecithin | 0.50 |
| Aspartame | 0.29 |
| Acesulfame-K | 0.05 |
| BHT | 0.02 |
| | 100.00 |

| ACETAMINOPHEN GUM | |
| --- | --- |
| INGREDIENT | PERCENTAGE |
| Sugar | 54.77 |
| Gum Base | 21.80 |
| Corn Syrup | 11.20 |
| Fructose | 5.60 |
| Glycerine | 3.40 |
| Acetaminophen | 1.70 |
| Flavors | 1.00 |
| Aspartame | 0.26 |
| Soluble Saccharin | 0.21 |
| Insoluble Saccharin | 0.06 |
| | 100.00 |

*5 gram chunk yields 85 mg acetaminophen
Formula can be modified to include caffeine.

By way of example, and not limitation, examples testing the chewing gum formulation of the present invention are as follows:

Experiment No. 1

Single dose, placebo controlled, randomized, two-way crossover study in 20 subjects to evaluate the effect of 50 mg caffeine gum compared to placebo gum-on positive and negative mood affects. Healthy subjects 18–65. Screening questionnaire to evaluate average caffeine consumption, tobacco drug and alcohol status. Any subjects taking medications with a CNS affect were excluded from the study. Approximately 2 hours on two occasions separated by at least 24 hours.

Dosing: 1×stick of caffeine gum to be chewed for 30 minutes. The chewing gum had the formulation set forth above in the table entitled caffeine gum.

The subjects were instructed that they were to have caffeine, alcohol or other drug use for at least 8 hours prior to test. No tobacco products for at least 2 hours prior to test. Subjects must have been awake and active for at least 8 but no more than 16 hours prior to starting the test. Subjects will be required to complete a 10 part questionnaire at the following time points (−20, −10, −5 and at 2, 5, 10, 15, 20, 30, 40 and 1 hour after starting to chew the gum. Appropriate analysis of comparison of each individual item of the test and grouped analysis for both positive and negative affect.

Data was corrected for baseline data (−5 minute reading) at each time point. Means and standard deviations for both active and placebo groups were evaluated for all time points.

Figure 1:
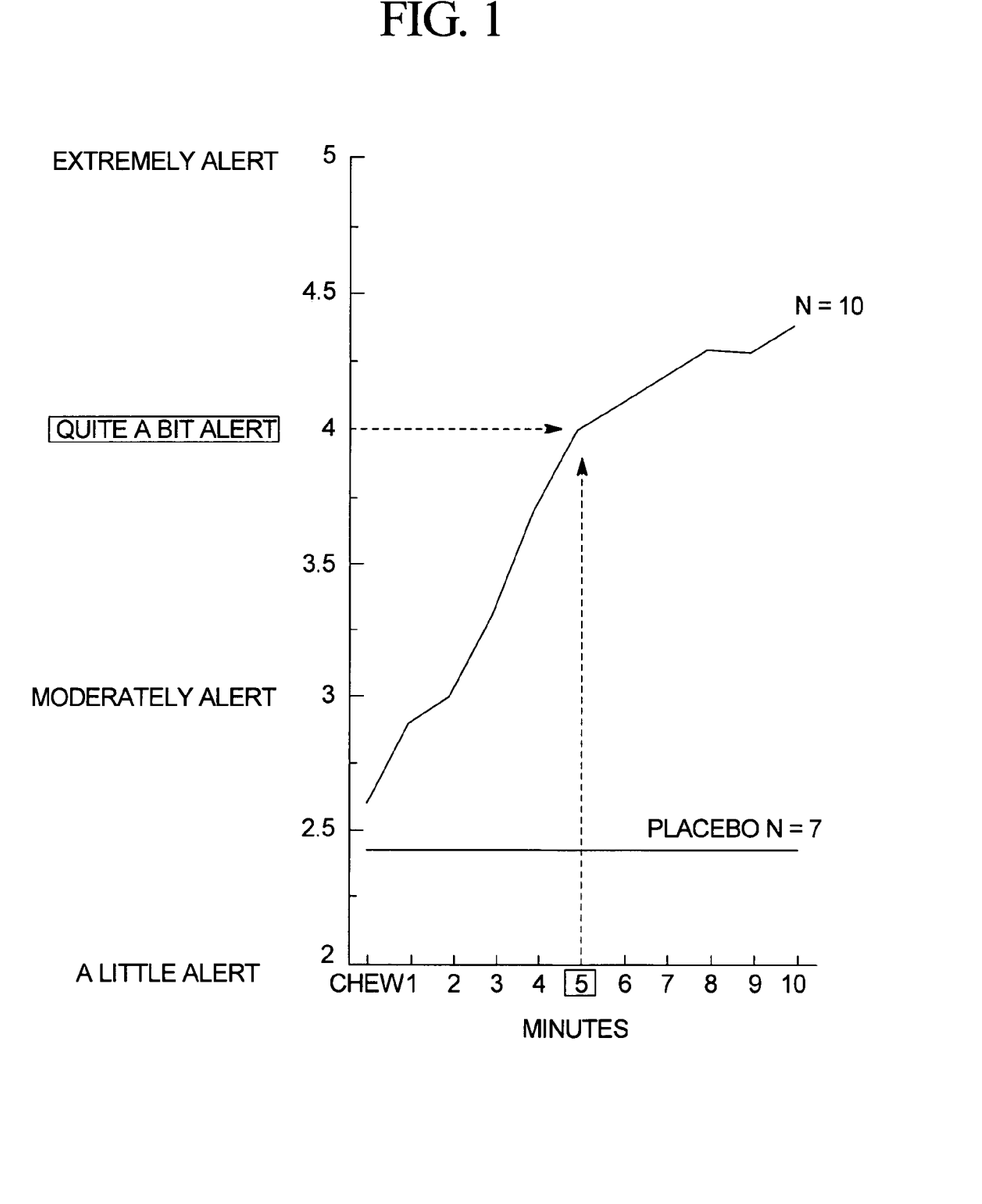
FIG. 1 illustrates graphically the results of Experiment No. 1 that is discussed supra.

The results of the analysis are set forth in FIG. 1. FIG. 1 graphically illustrates alertness versus time. These results demonstrate that by 5 minutes the subject reported that they were quite a bit alert. The alertness response was based on reference Panas feeling and emotion scale.

Experiment No. 2

A randomized, single-dose, two-way crossover study was conducted with six (6) healthy, adult, non-tobacco-using male subjects. A single 100 mg does of caffeine was administered in each study period after an overnight fast. The test treatment was two 50 mg caffeine chewing gum pieces (sticks), which were chewed for 15 minutes and removed. The reference treatment was one 100 mg chewable No-Doz® tablet, which was chewed and swallowed. One of the treatments was given in each period; the order of administration was according to the dosing randomization schedule. There was a 7-day washout between treatments.

Blood samples were collected pre-dose and over 15 hours after each dose. Plasma concentrations of caffeine were measured by a fully validated chromatographic procedure. Samples from subject with measurable pre-dose levels of caffeine were corrected for these levels. Pharmacokinetic parameters were calculated from the adjusted data and statistical analyses were performed to compare the test and reference treatments.

Clinical Procedures

A. Subject Selection.

The 6 subjects who participated in this study were healthy males, in the age range of 25 to 35 years, and within 15% of their ideal weight as specified in the protocol.

All subjects were selected based on the absence of any clinically significant findings on the medical history, physical examination, and clinical laboratory evaluations. Any laboratory value or vital sign measurement more than 10% outside the normal range was evaluated individually by the investigator. All were determined to be not clinically significant for those subjects enrolled in the study. All screening evaluations were performed within 28 days of initial dosing.

B. Drug Supplies.

| Formulations: | |
|---|---|
| Test (A) | Two 50 mg chewing gum sticks, Amurol Confections Co. (Lot #ALRT7/9/19/96, No exp. Date) |
| Reference (B) | One 100 mg No-Doz ® chewable table, Bristo-Myers Products (Lot #601041, Exp. date October 1998). |

Administration: The subjects received the test and reference after an overnight fast. The subjects randomized to the test first drank 240 ml of room temperature tap water. The chewing gum pieces were then chewed for 15 minutes and deposited into a labeled vial. The subjects randomized to the reference chewed the No-Doz® tablets and then drank 240 ml of room temperature tap water. The order of treatment administration was according to the randomization schedule.

All doses were administered at one-minute intervals beginning at 0700 hours. A thorough mouth check was performed to ensure that the chewable tablet was swallowed. A schedule of the actual dosing times, dates and treatment assignments is included in Table C2. All subjects remained under observation sitting upright or standing for at least two hours after each dosing. Six subjects were dosed in both Period I and Period II.

C. Study Conduct.

Confinement, Meals: During the confinement periods of this study, the subjects were housed and fed at the clinical facility.

In each period, the subjects reported for check-in (Day −1) at least 12 hours before dosing. Meals were provided on check-in day and completed at least 10 hours prior to scheduled dosing time. No food or beverages (except water) were permitted after 2100 hours on Day−1.

During confinement (Day 1), standardized, caffeine-free meals or snacks were served at 4, 10 and 14 hours after dosing, as specified on the Activity Schedule and Menu found in Section 3. The same menu was used during each study period. The subjects consumed at least 95% all food and beverages that were required. The subjects were released from the clinical facility approximately 2200 hours after dosing in each study period. A 7-day washout separated the dosings.

Restrictions: Prior to check-in for the study, the subjects were instructed to take no prescribed medications for at least 14 days prior to the initial dosing and throughout the study. No over-the-counter medications were permitted for 72 hours before dosing in each study period. No medications were permitted during confinement except those administered. Subjects were also instructed to abstain from any products containing alcohol or caffeine for 48 hours prior to dosing and throughout each confinement. None of the subjects reported taking any restricted substance within the time frame indicated.

During the confinement periods of the study, water was restricted from one hour before until one hour after dosing except for water (240 ml) administered with the dose. Water was permitted ad lib at all other times. Subjects remained sitting upright or standing for 2 hours after each dosing, except as required for study procedures. No strenuous physical exercise was permitted during confinement.

Safety: Urine drug screens were performed at each check-in to test for alcohol, marijuana and cocaine metabolites.

Blood pressure (sitting), pulse rate, respiratory rate and oral temperature were measured before each dosing. The investigator considered the measurements of all subjects as clinically acceptable for dosing.

Blood pressure and pulse rate measurements (sitting) were obtained approximately one hour after each dose and prior to release in each study period to monitor the health of the subjects. Measurements were repeated if clinically warranted.

A blood sample was collected at the time of the last sample of the study for a hematocrit determination. All hematocrit values were within 10% of the normal range (41–50%).

Adverse Events: The subjects were monitored throughout the study for any adverse experiences. They were encouraged to report signs, symptoms, and any changes in health to the study nurse. None of the subject reported any adverse events during this study.

Pharmacokinetic Samples: In each period, blood samples were collected prior to dosing and at the following nominal times after dosing: 0.25, 0.5, 1, 1.5, 2, 2.5, 3, 4, 6, 8, 10, 12 and 15 hours. The samples were labeled at the time of collection with a unique 6-digit code number. Pre-dose samples were collected within 30 minutes before dosing. All plasma samples were stored frozen between −18° C. and −20° C. until transfer to the laboratory for analysis, with the exception of one day.

Subject Completion: A total of 6 subjects were entered into the study and all subjects completed one study.

Analytical Procedures

A. Quality Control.

Standards and Controls: Calibration standards were prepared spiking a pool of human, interference-free, heparinized plasma with caffeine (USP Reference, Lot I). The plasma was obtained from Interstate Blood Bank (Memphis, Tenn.). The standards were prepared to contain 0.050, 0.100, 0.200, 0.500, 1.00, 2.00 and 5.00 μg/ml of caffeine.

The caffeine standards and controls were divided into 2.5 ml aliquots and stored in the laboratory in polypropylene snap-cap tubes frozen to at least −19° C.

The pre-study within-run coefficient of variation ranged from 0.915% to 2.54%. The relative accuracy of the procedure was estimated, through comparison of the measured concentration means of the control samples against their theoretical concentrations, and was found to average 99.5% for caffeine.

Run Acceptance Criteria: Chromatographic peak responses and peak response ratios were monitored using an electronic integrator. Each chromatographic tracing was inspected for acceptable retention times, peak shapes, resolution and integration before the peak response ratios (analyte-to-internal standard) were entered into the computer.

The acceptable limit of quantization for the run was evaluated through comparison of the mean response of the lowest concentration standards (0.050 μg/ml) with the responses of any interferences observed in the water blank, matrix blank and zero standard. The limit of quantization for the run was defined as the concentration at which the signal-to-noise ratio was at least 2.

Samples, standards and controls with an internal standard peak response which deviated more than ±25% from the mean within-run peak response of the internal standard (calculated for all standards and controls) were rejected.

The response ratio for each remaining non-zero standard was plotted as a function of concentration. A linear regression was calculated (R/S 1, version 4.3) by the method of least-squares using $(1/CONC)^2$ as a weighting factor. With this calibration line, a calculated concentration was determined for each standard sample. Any standard differing by more than ±25% from its theoretical value was excluded from the regression and the regression was recalculated. The analyte concentrations in the samples and the controls were estimated from the calibration line by use of the equation: (RATIO−INTERCEPT)/SLOPE.

The analytical run was considered acceptable if 4 of 6 controls passed established acceptance criteria and that at least one control sample was acceptable within each concentration range. Controls within an analytical run were considered acceptable if the low control values differed by no more than ±20% and the middle and high controls differed by no more than ±15% from their theoretical values. The concentrations o the controls were graphically displayed to permit visual confirmation of acceptability and identification of trends.

B. Sample Analysis.

Sample Storage and Stability: The plasma samples, which were collected in the clinic were transferred to the laboratory and stored frozen to at least −19° C. until analyzed. Samples were not identified to the analysts by treatment group. All subjects' samples were analyzed within 19 days of the initial sampling. The frozen stability of caffeine in plasma has been confirmed for 138 days.

Peak Identification: The retention times of the analyte and the internal standard were identified, in any given analytical run, by comparison to stock standards chromatographed at the beginning of the run and to processed standards chromatographed through the run.

Pharmacokinetic and Statistical Procedures

A. Pharmacokinetic Data.

All the available data from 6 subjects with reported caffeine concentrations were used in the pharmacokinetic analyses. Several subjects had pre-dose samples which contained measurable concentrations of caffeine. For each of these subject's data, the measured concentration at each sampling time was corrected by subtracting the level of caffeine at that time predicted from the decay of the pre-dose level. The decay curve was constructed using the elimination rate observed in the same period as the decay constant. After adjustment, each pre-dose level was 0.0 μg/ml, and each post-dose concentration was reduced accordingly.

Pharmacokinetic parameters (areas, times to peak, and elimination rates and half-lives) were calculated using the actual rather than the scheduled time of sample collection. Graphical presentations of individual subject results also used the exact times of sample collection. Graphical presentations of mean results used the scheduled times of sample collection.

Peak concentration (Cmax) was the observed maximum value (corrected for pre-dose levels, if necessary) during the collection period of 0 to 15 hours. The time to peak concentration (Tmax) was the time at which Cmax was observed (or first observed, if more than one peak was present).

The apparent first-order elimination rate (Ke) was estimated as the absolute value of the slope of the regression line for the terminal log-linear concentration-time values. The values included in the regression analyses were determined by examination of the individual subject plots of natural logarithm of concentration against time. Elimination half-life (t−½) was calculated as 0.693/Ke.

Area under the curve (AUC) to the time of the last non-zero concentration $(C_t)$ was calculated by the linear trapezoidal method. Area to infinite time (AUCinf) was calculated by extrapolating AUC by the addition of the quantity: $C_t/Ke$.

B. Statistical Analyses.

Statistical analyses were performed using the General Linear Models (GLM) procedures of the SAS statistical program. Hypothesis testing for treatment effects was conducted at α=0.05. The statistical model contained main effects of sequence, subject within sequence, period, and treatment. Sequence effects were tested against the type III mean square term for subjects within sequence. All other main effects were tested against the mean square error term.

The observed and calculated pharmacokinetic parameters as well as the caffeine concentrations at each of the individual collection times were compared statistically.

Power for the pair-wise pharmacokinetic comparisons was calculated as the probability (α=0.05) of detecting a difference equal to 20% of the mean for the reference treatment in the comparison, or a ratio of 1.25 for In-transformed results. [Winer, B J. *Statistical Principles In Experimental Design*. NEW YORK: McGraw-Hill Book Company (1962) 21–26.]

Confidence Intervals (90%) for pair-wise area and peak concentrations comparisons were calculated by the t-test approach (2,1-sided) at α=0.05 each side. The intervals were computed for the "true" mean test-to-reference treatment ratio (or geometric mean ratio for ln-transformed results).

Discussion and Results

Statistical analyses were performed on the caffeine data in order to compare the test chewing gum to the chewable reference tables. Natural log-transformation of the area and Cmax parameters was also performed and analyzed statistically. Table 1, which follows, summarizes the results (n=6) of the statistical analyses of the major bioavailability parameters.

Statistical comparisons of the test and reference formulations at each sampling time are summarized in Table 2.

Conclusion

The caffeine chewing gum pieces appear to have a much faster rate of absorption that the No-Doz® chewable tablets. The areas and peak concentrations of the chewing gum were less than half that of No-Doz®, and the time to reach a peak for the gum was 30 minutes earlier than for the tablet.

TABLE 1

Comparisons of caffeine results for 50 mg chewing gum pieces (Test) vs. 100 mg No-Doz ® chewable tablets (Reference) administered as a single 100 mg dose under fasting conditions to 6 subjects.

| Parameter | Least Squares Means[1] | | Test/Ref. Ratio[2] | Power[3] | 90% Confidence Interval[4] | |
|---|---|---|---|---|---|---|
| | Test | Reference | | | Lower | Upper |
| AUC 0-t (μg-hr/ml) | 7.26 | 17.65 | 0.412* | 0.50 | 0.246 | 0.577 |
| AUCinf (μg-hr/ml) | 9.60 | 23.72 | 0.405* | 0.39 | 0.211 | 0.598 |
| Cmax (μg/ml) | 0.92 | 2.15 | 0.429* | 0.76 | 0.309 | 0.548 |
| Tmax (hour) | 1.08 | 1.58 | 0.684 | 0.22 | — | — |
| Ke (1/hour) | 0.1241 | 0.1058 | 1.173* | 0.86 | — | — |
| Elimhalf (hour) | 5.97 | 6.97 | 0.857* | 0.86 | — | — |
| Ln-Transformed Data | | | | | | |
| AUC 0-t (μg-hr/ml) | 6.22 | 17.44 | 0.357* | 0.15 | 0.239 | 0.532 |
| AUCinf (μg-hr/ml) | 7.66 | 23.00 | 0.333* | 0.13 | 0.212 | 0.524 |
| Cmax (μg/ml) | 0.84 | 2.14 | 0.391* | 0.17 | 0.272 | 0.562 |

[1]Least squares geometric means for ln-transformed data.
[2]Test/Ref Ratio calculated as Test mean divided by Reference mean.
[3]Power to detect a difference of 20% (original data) or a ratio of 1.25 (ln-transformed data).
[4]Confidence interval on the ratio.
*Detected as statistically significant by ANOVA (α = 0.05).

TABLE 2

Summary of caffeine statistical comparisons at each sampling time comparing 50 mg chewing gum pieces (Test) vs. 100 mg No-Doz ® chewable tablets (Reference) administered as a single 100 mg dose under fasting conditions to 6 subjects.

| Sample Time | Collection (Hour) | Least Squares Means (μg/ml) | | Significance* |
|---|---|---|---|---|
| | | Test | Reference | |
| 1 | Pre-dose | 0.00 | 0.00 | — |
| 2 | 0.25 | 0.23 | 0.36 | 0.0269 |
| 3 | 0.50 | 0.79 | 1.18 | None |
| 4 | 1.00 | 0.83 | 1.91 | 0.0008 |
| 5 | 1.50 | 0.84 | 2.05 | 0.0006 |
| 6 | 2.00 | 0.75 | 2.01 | 0.0004 |
| 7 | 2.50 | 0.72 | 1.92 | 0.0001 |
| 8 | 3.00 | 0.68 | 1.78 | 0.0006 |
| 9 | 4.00 | 0.66 | 1.64 | 0.0006 |
| 10 | 6.00 | 0.57 | 1.33 | 0.0046 |
| 11 | 8.00 | 0.47 | 1.10 | 0.0088 |
| 12 | 10.00 | 0.37 | 0.90 | 0.0052 |
| 13 | 12.00 | 0.28 | 0.75 | 0.0021 |
| 14 | 15.00 | 0.22 | 0.56 | 0.0068 |

*Statistical comparisons to test for the equivalence of treatment effects were performed at an α level of 0.05. The actual p-value is indicated at the time where statistically significant differences (p < 0.05) were detected; "None" indicates that no significance was detected (p < 0.05) at that time.

Figure 2:
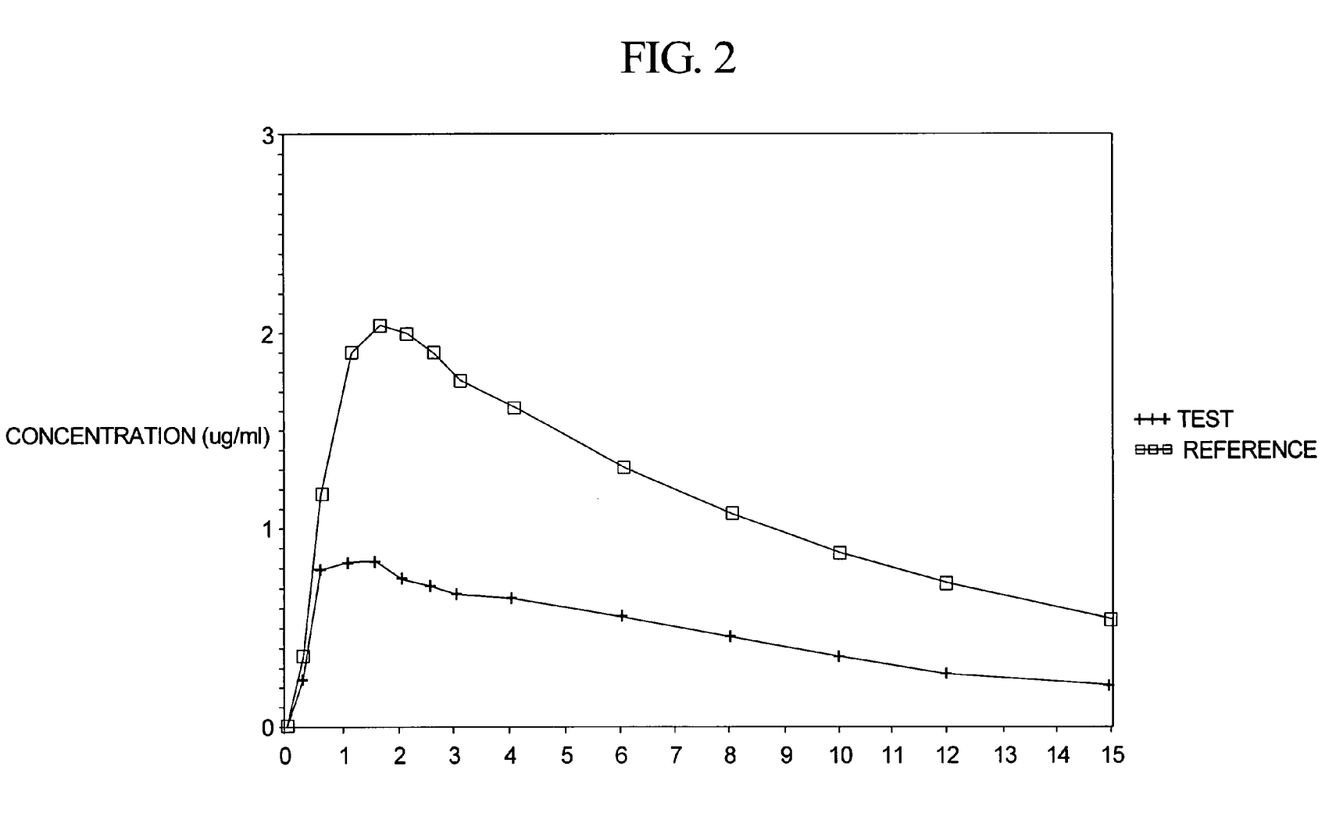
FIG. 2 illustrates graphically the results of Experiment No. 2 that is discussed supra.

FIG. 2 illustrates graphically least squares mean plasma concentration (~=6). Concentration of caffeine in (reg/ml) versus hours of the dose is illustrated graphically; chewing gum provided 50 mg of caffeine versus 100 mg of No-Doz® tablet. It should be noted that although in FIG. 2 the blood concentration level of caffeine is approximately 50% that of No-Doz®, the amount of caffeine delivered by the chewing gum was 50% that of the No-Doz®.

Experiment No. 3

The following protocol was followed. The chewing gum formula set forth on page 15 under the heading caffeine gum was used. Subjects chewed gum for 5 minutes. Then, the gum cuds were then collected and analyzed for caffeine. At T-10 minutes, the gum was collected after chewing for 10 minutes and then had the caffeine analyzed. This was. repeated for all the time figures up to time 60 minutes. "Times 0" refers to non-chewed gum product. All these T-0 to T-60 minute gum samples were from the same lot of chewing gum.

The results are as follows:

TABLE 3

| Timed Chewed Minutes | Mg Caffeine remaining in gum | Actual % Caffeine remaining in gum | Relative % Caffeine remaining in gum |
|---|---|---|---|
| $T_0$ | 57.96 | 2.07 | 100.00 |
| $T_5$ | 16.80 | 0.60 | 28.70 |
| $T_{10}$ | 7.56 | 0.27 | 12.98 |
| $T_{20}$ | 1.68 | 0.06 | 3.01 |
| $T_{30}$ | 0.84 | 0.03 | 1.32 |
| $T_{40}$ | 0.00 | 0.00 | 0.00 |
| $T_{60}$ | 0.00 | 0.00 | 0.00 |

Figure 3:
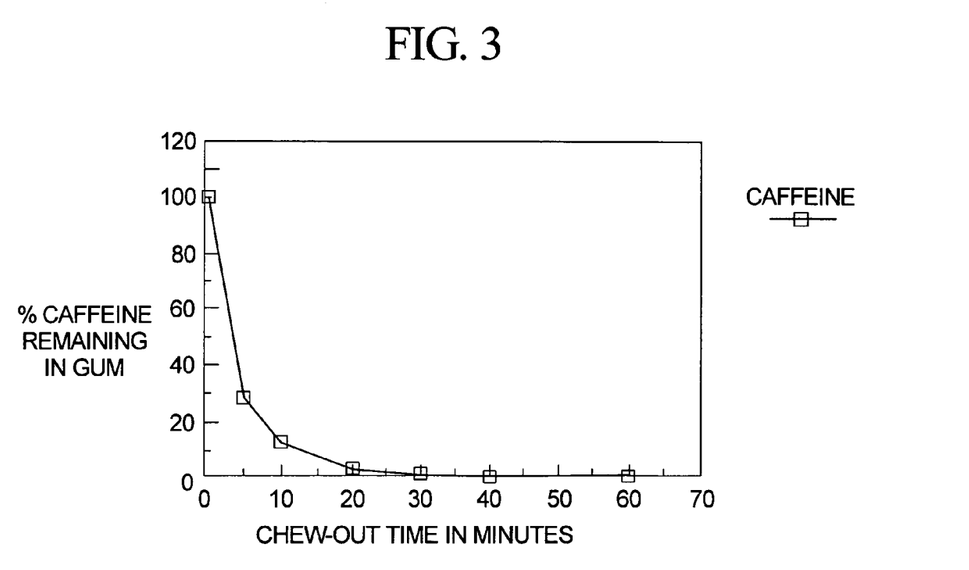
FIG. 3 illustrates graphically the results of Experiment No. 3 that is discussed supra.

FIG. 3 illustrates graphically % caffeine remaining over chew-out time in minutes.

Experiment No. 4

To detect adsorption in the oral cavity, the following experiment was carried out.

Samples of Stay-Alert Cinnamon flavored caffeine gum (Lot 713176) were analyzed for caffeine and found to contain 53.44±0.52 mg per stick. Two subject (S1 and S2) were recruited to chew the gum. Each subject chewed one stick of gum for 20 minutes, expectorating all saliva into a container. After chewing, each rinsed twice with 10 ml of water (20 ml total) and added the rinse water to the collected saliva. The volume of this solution was brought up to 75 ml with distilled water. S2 repeated the extraction process with a new stick of gum.

The chewed gum cuds and the saliva solutions were analyzed for caffeine by gas chromatography. (A spiking study was also conducted which showed recovery of caffeine from gum cuds and saliva solutions to be 99.25% and 103.50% respectively. Measured caffeine levels were not corrected for these recoveries as they were not deemed significantly different from 100%.) The results of the experiment are reported in Table 4.

TABLE 4

|  | S1 | S2a | S2b |
|---|---|---|---|
| Volume of Saliva (ml) | 50 | 30 | 30 |
| Initial caffeine level (mg) | 53.44 | 53.44 | 53.44 |
| Caffeine remaining in cud (mg) | 2.00 | 13.09 | 15.12 |
| Caffeine in Saliva (mg) | 45.69 | 30.26 | 28.97 |
| Total Caffeine recovered (mg) | 47.69 | 43.35 | 44.09 |
| Unrecovered caffeine (mg) | 5.75 | 10.09 | 9.35 |
| Percent of released unrecovered | 11.2 | 25.0 | 24.4 |

It is believed that the unrecovered caffeine was adsorbed through mucous membranes in the oral cavity. Thus between 11 and 25% of the released caffeine was adsorbed orally. Note that the higher concentration of caffeine in saliva for S2 may have contributed to the higher adsorption in that subject.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

We claim:

1. A method of enhancing an individual's performance comprising the steps of:
   providing a chewing gum including an amount of caffeine that is designed to be adsorbed through the oral mucosa of the individual;
   chewing the chewing gum to thereby causing the caffeine to release into the saliva of the individual;
   chewing the chewing gum ten minute or less before the performance to create a saliva content of caffeine from about 15 ppm to about 440 ppm; and
   continuing to chew the chewing gum to force absorbing the saliva content of caffeine through the oral mucosa and into the systemic system of the individual.

2. The method of claim 1 wherein the performance to be enhanced is athletic.

3. The method of claim 1 wherein the performance to be enhanced is cognitive.

4. The method of claim 1 wherein the performance to be enhanced is alertness.

5. The method of claim 1 wherein the chewing gum is chewed five minutes or less before the performance.

* * * * *